US00PP18114P3

(12) United States Plant Patent

Cain et al.

(10) Patent No.: US PP18,114 P3

(45) Date of Patent: Oct. 9, 2007

(54) NECTARINE TREE NAMED 'SUNECTWENTYONE'

(50) Latin Name: ***Prunus persica* var. *nucipersica***
Varietal Denomination: Sunectwentyone

(75) Inventors: David W. Cain, Bakersfield, CA (US); Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 55 days.

(21) Appl. No.: 11/329,211

(22) Filed: Jan. 10, 2006

(65) Prior Publication Data

US 2007/0163013 P1 Jul. 12, 2007

(51) Int. Cl.
*A01H 5/00* (2006.01)

(52) U.S. Cl. ..... Plt./190

(58) Field of Classification Search ..... Plt./190
See application file for complete search history.

(56) References Cited

U.S. PATENT DOCUMENTS

PP7,305 P 8/1990 Zaiger et al.

*Primary Examiner*—Kent Bell
*Assistant Examiner*—Annette H Para
(74) *Attorney, Agent, or Firm*—Knobbe, Martens, Olson & Bear, LLP

(57) ABSTRACT

A new and distinct nectarine tree variety, *prunus persica* var. 'Sunectwentyone' that possesses a relatively low chilling requirement of 250 hours at or below 7.2° C.; heavy production of relatively large (66 mm), very firm fruit that can be harvested about May 8–15 in Kern County, Calif., (about 4 days after 'April Glo' nectarine (U.S. Plant Pat. No. 7305)). The nectarine fruit is bright red with bright yellow flesh that is moderately juicy, very firm, and tart-sweet with 12 brix. The plant has a relatively low tendency for split-pits, russeting, and thrips damage.

1 Drawing Sheet

Figure 1:
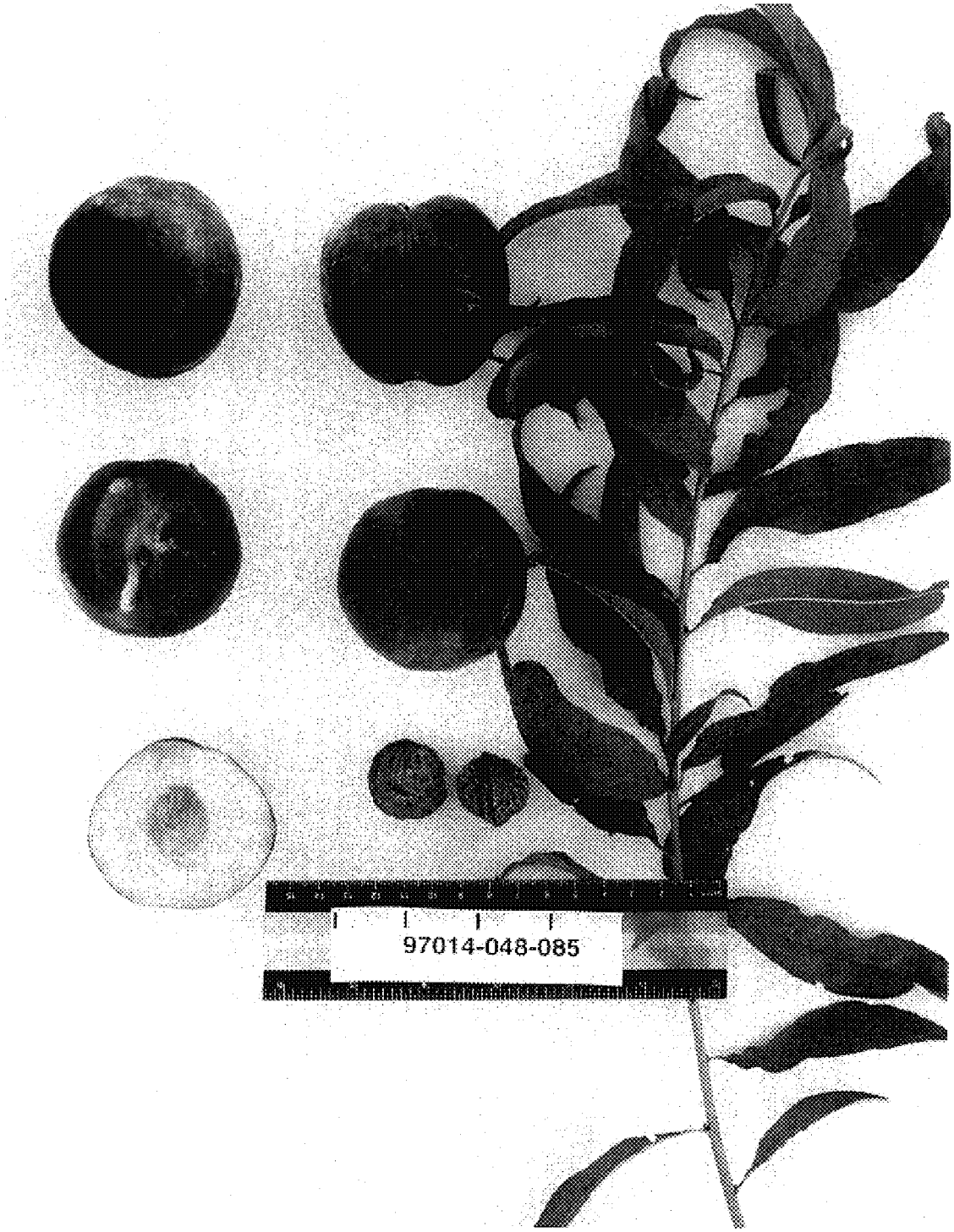

Latin name of the genus and species: *Prunus persica* var. *nucipersica*.
Variety denomination: 'Sunectwentyone'.

BACKGROUND AND SUMMARY OF THE INVENTION

This invention relates to the discovery and asexual propagation of a new and distinct variety of nectarine tree, *Prunus persica* var. *nucipersica,* cv. 'Sunectwentyone.' The new variety was first hybridized and selected as '97014-048-085' by David Cain. The new variety was first selected and evaluated by David Cain and Terry Bacon near Mecca, Calif. in Riverside County during April, 1999.

The new variety 'Sunectwentyone' is characterized by having heavy production of relatively large (66 mm), very firm fruit. The bright red fruit has bright yellow flesh that is moderately juicy, very firm, and tart-sweet with approximately 12 brix. 'Sunectwentyone' has a relatively low chilling requirement of 250 hours at or below 7.2° C. The new variety has a relatively low tendency for split-pits, russeting, and thrips damage. The fruit is typically harvested about May 8–15 in Kern County, Calif., with the harvest starting about 4 days after the harvest date of 'April Glo' (U.S. Plant Pat. No. 7,305) nectarine variety.

The seed parent of the new variety is '94-051N' (unpatented) which was selected from a progeny of a cross between two breeding selections; an unknown low-chill nectarine crossed with pollen of 'FLA85-1' peach (unpatented). The pollen parent is '94-025N' (unpatented) that was selected from a progeny of a cross between two low-chill breeding selections; 'FLA88-16N' nectarine (unpatented) crossed with pollen of 'FLA9-20C' peach (unpatented). The parent varieties were first crossed in 1997 with the date of planting of January 1998 and the date of first flowering being January 1999.

The new nectarine variety 'Sunectwentyone' was first asexually propagated by David Cain near Wasco, Kern County, Calif. in 1999 by budding onto 'Flordaguard' (unpatented) rootstock. The new variety 'Sunectwentyone' has been shown to maintain its distinguishing characteristics through successive asexual propagations.

The new variety 'Sunectwentyone' is distinguished from its seed parent, '94-051N' in that 'Sunectwentyone' ripens approximately 5 days later than '94-051N.' Further, the fruit of the new variety is larger than the fruit of '94-051N' (66 mm compared to 64 mm).

The new variety 'Sunectwentyone' is distinguished from its pollen parent, '94-025N' in that 'Sunectwentyone' ripens approximately 14 days earlier than '94-025N.'

The new nectarine variety 'Sunectwentyone' can be distinguished from presently available cultivars in commerce by the following combination of characteristics: the new 'Sunectwentyone' most nearly resembles 'April Glo' nectarine in ripening time, but 'Sunectwentyone' begins harvest about 4 days later and has larger fruit (66 mm compared to 58 mm for 'April Glo').

BRIEF DESCRIPTION OF THE PHOTOGRAPH

The accompanying color photographic illustration (FIG. 1) shows typical specimens of the foliage and fruit of the new nectarine variety 'Sunectwentyone.' The illustration shows the upper and lower surface of the leaves, an exterior and sectional view of a fruit divided across its suture plane to show flesh color, pit cavity and the stone remaining in place. The photographic illustration was taken shortly after being picked (shipping ripe) and the colors are as nearly true as is reasonably possible in a color representation of this type.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England.

The descriptive matter which follows pertains to 4-year-old 'Sunectwentyone' plants grown on 'Flordaguard' rootstock in the vicinity of Wasco, Kern County, Calif., during 2003, and is believed to apply to plants of the variety grown under similar conditions of soil and climate elsewhere.

The new variety 'Sunectwentyone' has not been observed under all possible environmental conditions. The phenotype may vary somewhat with variations in environment such as temperature, daylength, and light intensity, without, however, any variance in genotype.

TREE

General: (Measurements taken on 4 year old tree unless otherwise noted.).

*Size.*—Large. Normal for most nectarine varieties. Reaches a height of approximately 3.2 meters including normal pruning.

*Vigor.*—Vigorous; growth of approximately 1.8 to 2 meters height the first growing season.

*Growth.*—Upright-spreading.

*Productivity.*—Productive. Fruit set is usually two or more times desired amount for marketable size fruit. Thinning and spacing of fruit is necessary.

*Form.*—Vase formed.

*Bearer.*—Regular. No alternate bearing observed.

*Fertility.*—Self-fertile.

*Canopy density.*—Dense. Pruning is required to open tree vase shape, allowing more sunlight to center of tree.

*Hardiness.*—Hardy in all fruit growing areas of California. Winter chilling requirement is approximately 250 hours at or below 7.2° C.

*Disease resistance/susceptibility.*—No specific testing for relative plant disease resistance/susceptibility has been designed. Under close observation in Wasco, Kern County, Calif., no particular plant/fruit disease resistance/susceptibility has been observed.

Trunk: (Measurements at approximately 30 cm above soil line.).

*Diameter.*—Approximately 22 cm. Varies with soil type, fertility, climatic conditions and cultural practices.

*Texture.*—Medium shaggy, increases with age of tree.

*Color.*—About Greyed-green 198D to Greyed-red 178A. Becomes darker with age.

Branches: (Measurements at approximately 90 cm above soil line.).

*Diameter.*—Ranges from approximately 8 cm to approximately 10 cm.

*Texture.*—Smooth on 1st year wood, increasing roughness with tree age.

*Color.*—Branches vary from about Greyed-orange 166A to Greyed-green 198D.

*Lenticels.*—Number: Numerous. Approximately 1.3 per square centimeter. Color: About Greyed-orange 164B. Typical size: Approximately 7 mm in length and approximately 2 mm wide.

Flowering shoots: (Data taken in July at midpoint of current-season growth.).

*Diameter.*—Approximately 5 mm.

*Color.*—Topside: About Grey-brown 199A to Green 141B. Underside: About Green 141B.

*Lenticels.*—None observed.

*Leaf buds.*—Shape: Obovate. Width: Approximately 2 mm. Length: Approximately 3 mm. Color: About Greyed-orange 165A.

*Flower buds.*—Shape: Obovate. Width: Approximately 2.5 mm. Length: Approximately 4 mm. Color: About Greyed-orange 165A. Number of buds per node: Usually 2.

LEAVES (Data taken in July on fully expanded leaf at midpoint of current-season growth.).

*Length.*—Approximately 160 mm.

*Width.*—Approximately 38 mm.

*Thickness.*—Medium.

*Color.*—Upper surface: About Green 135B. Lower surface: About Green 137D.

*Form.*—Lanceolate.

*Tip.*—Acuminate.

*Base.*—Acuminate.

*Margin.*—Lightly crenate.

*Venation.*—Pinately net veined.

*Vein color.*—Approximately Yellow-green 148C.

*Surface texture.*—Smooth.

*Petiole.*—Average length: Approximately 8 mm. Average diameter: Approximately 2 mm. Color: About Yellow-green 146C.

*Stipules.*—Number: 2 per leaf bud when present. Typical length: Approximately 8 mm. Color: Approximately Green 135B.

*Glands.*—Form: Reniform. Number: Varies from about 2 to 4. Position: Alternate on upper portion of petiole and base of leaf blade. Average size: Approximately 1.5 mm by 1 mm. Color: About Yellow-green 146C.

FLOWERS (fully opened)

General:

*Blooming period.*—First bloom: Approximately Feb. 2, 2003. Full bloom: Approximately Feb. 12, 2003.

*Duration.*—Typically about 10 days from first bloom to petal fall in the Central San Joaquin Valley. Varies widely depending on temperatures during bloom and conditions prior to bloom.

*Type.*—Non-showy.

*Diameter.*—Approximately 32–35 mm.

Peduncle:

*Length.*—Approximately 3–4 mm.

*Diameter.*—Approximately 2 mm.

*Color.*—About Yellow-green 146C.

Petals:

*Number.*—5.

*Arrangement.*—Free.

*Length.*—Approximately 14–16 mm.

*Diameter.*—Approximately 9–12 mm.

*Shape.*—Broadly ovate.

*Apex shape.*—Rounded.
*Base shape.*—Narrows at point of attachment.
*Color.*—About Red-purple 63A when newly opened, darkening with advanced senescence.
*Surface texture.*—Smooth.
*Margins.*—Smooth, Undulating.

Sepals:
*Number.*—5.
*Length.*—Approximately 5 mm.
*Diameter.*—Approximately 4 mm.
*Shape.*—Ovate.
*Color.*—About Greyed-red 178A.
*Surface texture.*—Smooth.

Stamens:
*Number.*—Approximately 30 to 40, average 38.
*Average length.*—Approximately 13 mm
*Filament color.*—About Red-purple 62D.
*Anther color (just prior to dehiscence).*—About Yellow-orange 17B.
*Pollen Color.*—About Yellow-orange 17B.

Pistil:
*Number.*—Usually one, occasionally two.
*Average length.*—Approximately 16–19 mm.
*Ovary diameter.*—Approximately 3 mm.
*Pubescence.*—None.
*Position.*—Stigma extends slightly above anthers.

Aroma: Very slight.

FRUIT (Data taken at firm-ripe on mature tree managed to obtain maximum quality under conditions stated in Description of Variety.).

General:
*Fruit harvest.*—Date of first pick: May 7, 2003. Date of last pick: May 15, 2003.

Size: (Under conditions typical of the San Joaquin Valley, Calif.).
*Length (stem end to apex).*—Approximately 65 mm.
*Diameter in line with suture plane.*—Approximately 66 mm.
*Diameter perpendicular to suture plane.*—Approximately 66 mm.
*Average weight.*—Approximately 160 gm.

Form:
*Viewed from apex.*—Round, nearly symmetrical.
*Viewed from side, facing suture.*—Rounded, slightly elongated, slightly raised shoulders, nearly symmetrical.
*Viewed from side, perpendicular to suture.*—Rounded, slightly elongated, nearly symmetrical.

Apex shape: Slightly indented in most years.

Stem-end cavity depth: Shallow.

Stem:
*Length.*—Approximately 8 mm.
*Diameter.*—Approximately 2.5 mm.
*Color.*—About Greyed-orange 164B.

Skin:
*Thickness.*—Medium.
*Adherence to flesh.*—Tenacious.
*Surface texture.*—Smooth.
*Pubescence.*—None.
*Ground color.*—About Yellow 11A with slight green background when mature.
*Overcolor.*—About Red 45D when mature, covers 85–95% of fruit surface.
*Taste.*—Neutral.

Flesh:
*Ripens.*—Evenly.
*Texture.*—Very firm, fine.
*Fibers.*—Few, short.
*Flavor.*—Tart-sweet.
*Brix.*—Approximately 12 degrees.
*Juice.*—Moderate.
*Aroma.*—None observed.
*Color.*—Yellow, about Yellow 11B.

Pit cavity:
*Color.*—About Yellow 11B.
*Size.*—Length: Approximately 30 mm. Diameter in line with suture: Approximately 31 mm. Diameter perpendicular to suture: Approximately 27 mm.

Use: Dessert. Market, local and long distance.

Shipping/keeping quality: Good. Holds well in cold storage for approximately 4 weeks and maintains good firmness and eating quality. Minimal bruising and scarring in packing and shipping trials.

Stone: (Measurements taken on dried stones.).
*Freeness.*—Clingstone.
*Size.*—Length: Approximately 30 mm. Diameter in line with suture plane: Approximately 31 mm. Diameter perpendicular to suture plane: Approximately 27 mm.
*Form (viewed from side).*—Nearly round and symmetrical.
*Form (viewed from stem end).*—Nearly round and symmetrical.
*Base shape.*—Rounded and retuse at stem attachment.
*Apex shape.*—Rounded with a small, sharp point.
*Surface.*—Irregularly furrowed throughout. Heavily ridged throughout. Heavily pitted throughout.
*Halves.*—Nearly equal.
*Ridges.*—2 on each side of the suture, rounded beginning at the base and extending throughout the length of the stone.
*Outgrowing keel.*—Partially developed.
*Tendency to split.*—None.
*Color.*—About Greyed-orange 166D when dried.

What is claimed is:

1. A new and distinct nectarine tree as herein described and illustrated.

* * * * *